US00PP24621P2

(12) United States Plant Patent
Post

(10) Patent No.: US PP24,621 P2
(45) Date of Patent: Jul. 8, 2014

(54) ***CHRYSANTHEMUM* PLANT NAMED 'DELIALDONZE'**

(50) Latin Name: *Chrysanthemum×morifolium*
Varietal Denomination: Delialdonze

(75) Inventor: Arie Gerard Post, Naaldwijk (NL)

(73) Assignee: Deliflor Royalties B.V., Maasdijk (NL)

( * ) Notice: Subject to any disclaimer, the term of this patent is extended or adjusted under 35 U.S.C. 154(b) by 169 days.

(21) Appl. No.: 13/507,246

(22) Filed: Jun. 14, 2012

(51) Int. Cl.
*A01H 5/00* (2006.01)

(52) U.S. Cl.
USPC ..... Plt./297

(58) Field of Classification Search
CPC ..... A01H 5/0255
USPC ..... Plt./297
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Delialdonze' characterized by its upright and uniform plant habit; vigorous growth habit; strong flowering stems; freely branching habit; early and freely flowering habit; uniform flowering response; semi-double-type inflorescences with pink-colored ray florets and light green-colored disc florets; and good postproduction longevity.

2 Drawing Sheets

Botanical designation: *Chrysanthemum×morifolium*.
Cultivar denomination: 'DELIALDONZE'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Delialdonze'.

The new *Chrysanthemum* plant is a product of a planned breeding program conducted by the Inventor in Maasdijk, The Netherlands. The objective of the breeding program is to create new vigorous semi-double-type *Chrysanthemum* plants with attractive ray floret coloration and excellent post-production longevity.

The new *Chrysanthemum* plant originated from a cross-pollination made by the Inventor in Maasdijk, The Netherlands in March, 2005 of a proprietary selection of *Chrysanthemum×morifolium* identified as code number DB 10220, not patented, as the female, or seed, parent with a proprietary selection of *Chrysanthemum×morifolium* identified as code number DB 9992, not patented, as the male, or pollen, parent. The new *Chrysanthemum* plant was discovered and selected by the Inventor as a single flowering plant from within the progeny of the stated cross-pollination in a controlled greenhouse environment in Maasdijk, The Netherlands in June, 2006.

Asexual reproduction of the new *Chrysanthemum* plant by terminal cuttings in a controlled greenhouse environment in Maasdijk, The Netherlands since June, 2006, has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural practices. The phenotype may vary somewhat with variations in environment such as temperature, daylength and light intensity, without, however, any variance in genotype.

The following traits have been repeatedly observed and are determined to be the unique characteristics of 'Delialdonze'. These characteristics in combination distinguish 'Delialdonze' as a new and distinct *Chrysanthemum* plant:

1. Upright and uniform plant habit.
2. Vigorous growth habit.
3. Strong flowering stems.
4. Freely branching habit.
5. Early and freely flowering habit.
6. Uniform flowering response.
7. Semi-double-type inflorescences with pink-colored ray florets and light green-colored disc florets.
8. Good postproduction longevity.

Plants of the new *Chrysanthemum* differ from plants of the female parent selection in the following characteristics:

1. Plants of the new *Chrysanthemum* flower earlier than plants of the female parent selection.
2. Plants of the new *Chrysanthemum* have larger inflorescences than plants of the female parent selection.

Plants of the new *Chrysanthemum* differ from plants of the male parent selection in the following characteristics:

1. Plants of the new *Chrysanthemum* have larger inflorescences than plants of the male parent selection.
2. Plants of the new *Chrysanthemum* and the male parent selection differ in ray floret color as plants of the male parent selection have white-colored ray florets.

Plants of the new *Chrysanthemum* can be compared to plants of *Chrysanthemum×morifolium* 'Leon', disclosed in U.S. Plant Pat. No. 17,429. In side-by-side comparisons conducted in Maasdijk, The Netherlands, plants of the new *Chrysanthemum* differed from plants of 'Leon' in the following characteristics:

1. Plants of the new *Chrysanthemum* had fewer inflorescences per flowering stem than plants of 'Leon'.
2. Disc florets of plants of the new *Chrysanthemum* were light green in color whereas disc florets of plants of 'Leon' were yellow green in color.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Delialdonze' grown as a spray type.

The photograph on the second sheet comprises close-up views of the upper (top of the photographic sheet) and lower surfaces (bottom of photographic sheet) of typical inflorescences and leaves of 'Delialdonze'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of cut *Chrysanthemum* production. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7,000 lux. Plants were nine weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Delialdonze'.

Parentage:

*Female, or seed, parent*.—Proprietary selection of *Chrysanthemum×morifolium* identified as code number DB 10220, not patented.

*Male, or pollen, parent*.—Proprietary selection of *Chrysanthemum×morifolium* identified as code number DB 9992, not patented.

Propagation:

*Type*.—Terminal vegetative cuttings.

*Time to initiate roots, summer*.—About four days at 20° C.

*Time to initiate roots, winter*.—About six days at 20° C.

*Time to produce a rooted young plant, summer*.—About 13 days at 20° C.

*Time to produce a rooted young plant, winter*.—About 15 days at 20° C.

*Root description*.—Fine, fibrous; light brown in color.

*Rooting habit*.—Freely branching, moderately dense.

Plant description:

*Plant and growth habit*.—Herbaceous semi-double-type cut flower that is typically grown as a spray-type; upright and uniform plant habit; vigorous growth habit.

*Flowering stem description*.—Aspect: Erect. Length: About 85 cm. Spray diameter: About 20 cm. Diameter: About 6 mm. Lateral branch length: About 5 cm to 10 cm. Lateral branch diameter: About 2 cm to 5 cm. Internode length: About 2 cm to 3 cm. Strength: Strong. Texture: Pubescent; longitudinally ridged. Color: Close to 146C.

*Foliage description*.—Arrangement: Alternate; simple. Length: About 7 cm to 11 cm. Width: About 5 cm to 8 cm. Shape: Roughly ovate, palmately lobed. Apex: Mucronulate. Base: Attenuate. Margin: Palmately lobed, serrate; sinuses parallel to convergent. Texture, upper and lower surfaces: Pubescent, slightly rough; veins prominent on lower surface. Venation pattern: Pinnate, reticulate. Color: Developing leaves, upper surface: Close to N137C. Developing leaves, lower surface: Close to 147B. Fully developed leaves, upper surface: Close to N137B; venation, close to 147B. Fully developed leaves, lower surface: Close to 147B; venation, close to 147C. Petiole: Length: About 2 cm to 2.5 cm. Diameter: About 3 mm to 4 mm. Texture, upper and lower surfaces: Pubescent, slightly rough. Color, upper surface: Close to 147B. Color, lower surface: Close to 147C.

Inflorescence description:

*Appearance*.—Semi-double type inflorescence form with oblong-shaped ray florets; inflorescences borne on terminals, arising from leaf axils; ray and disc florets develop acropetally on a capitulum.

*Fragrance*.—Moderately fragrant.

*Flowering response*.—Under natural conditions, plant flower in the autumn and winter in the Northern Hemisphere; at other times of the year, inflorescence initiation and development can be induced under short day/long night conditions (at least 13.5 hours of darkness); early and uniform flowering response; plants exposed two weeks of long day/short night conditions after planting followed by photoinductive short day/long night conditions flower about 47 days later when grown as a spray-type.

*Postproduction longevity*.—In an interior environment, inflorescences and foliage will maintain good color and substance for about two weeks; inflorescences persistent.

*Quantity of inflorescences*.—Freely flowering habit; when grown as a spray type, about twelve inflorescences develop per flowering stem.

*Inflorescence size*.—Diameter: About 7 cm. Depth (height): About 1 cm to 1.5 cm. Disc diameter: About 1.5 cm. Receptacle height: About 6 mm. Receptacle diameter: About 6 mm to 8 mm. Receptacle color: Close to 145B.

*Inflorescence buds*.—Height: About 3 mm to 4 mm. Diameter: About 8 mm. Shape: Flattened spherical. Color: Close to 137C and 149D.

*Ray florets*.—Length: About 2.5 cm to 3 cm. Width: About 1.5 cm. Shape: Oblong. Apex: Rounded to emarginate. Base: Attenuate. Margin: Entire. Angle: Initially upright to close to perpendicular to the peduncle with development. Texture, upper and lower surfaces: Smooth, glabrous; satiny. Number per inflorescence: About 20 arranged in about two whorls. Color: When opening, upper surface: Between 75B and 75D. When opening, lower surface: Close to 75D. Fully opened, upper surface: Close to 75C; color becoming closer to between 75C and 75D with development. Fully opened, lower surface: Close to 75D.

*Disc florets*.—Shape: Fused tubular, elongated. Apex: Dentate. Length: About 6 mm. Diameter: About 1.5 mm. Number per inflorescence: About 250 massed at the center of the receptacle. Color, immature: Apex: Close to 145A. Mid-section: Close to 15C. Base: Close to 145D. Color, mature: Apex: Close to 145D. Mid-section: Close to 145C to 145D. Base: Close to 145C.

*Involucral bracts*.—Length: About 6 mm to 10 mm. Width: About 3 mm to 6 mm. Shape: Ovate. Apex: Rounded. Base: Rounded to truncate. Margin: Entire. Texture, upper and lower surfaces: Smooth, glabrous. Number per inflorescence: About 30 arranged in about two to three whorls. Color, upper surface: Close to 137B. Color, lower surface: Close to N137C.

*Peduncles*.—Length, fourth peduncle: About 10 cm. Length, seventh peduncle: About 12 cm. Diameter: About 3 mm. Angle: About 30° from vertical. Strength: Strong. Texture: Pubescent; longitudinally ridged. Color: Close to 146A.

*Reproductive organs*.—Androecium: Not observed. Gynoecium: Present on both ray and disc florets. Style length: About 6 mm. Style color: Greenish. Stigma color: Yellowish.

*Seeds and fruits*.—Seed and fruit production has not been observed on plants of the new *Chrysanthemum*.

Disease & pest resistance: Plants of the new *Chrysanthemum* have not been observed to resistant to pathogens and pests common to *Chrysanthemum* plants grown under commercial production conditions.

It is claimed:

1. A new and distinct *Chrysanthemum* plant named 'Delialdonze' as illustrated and described.

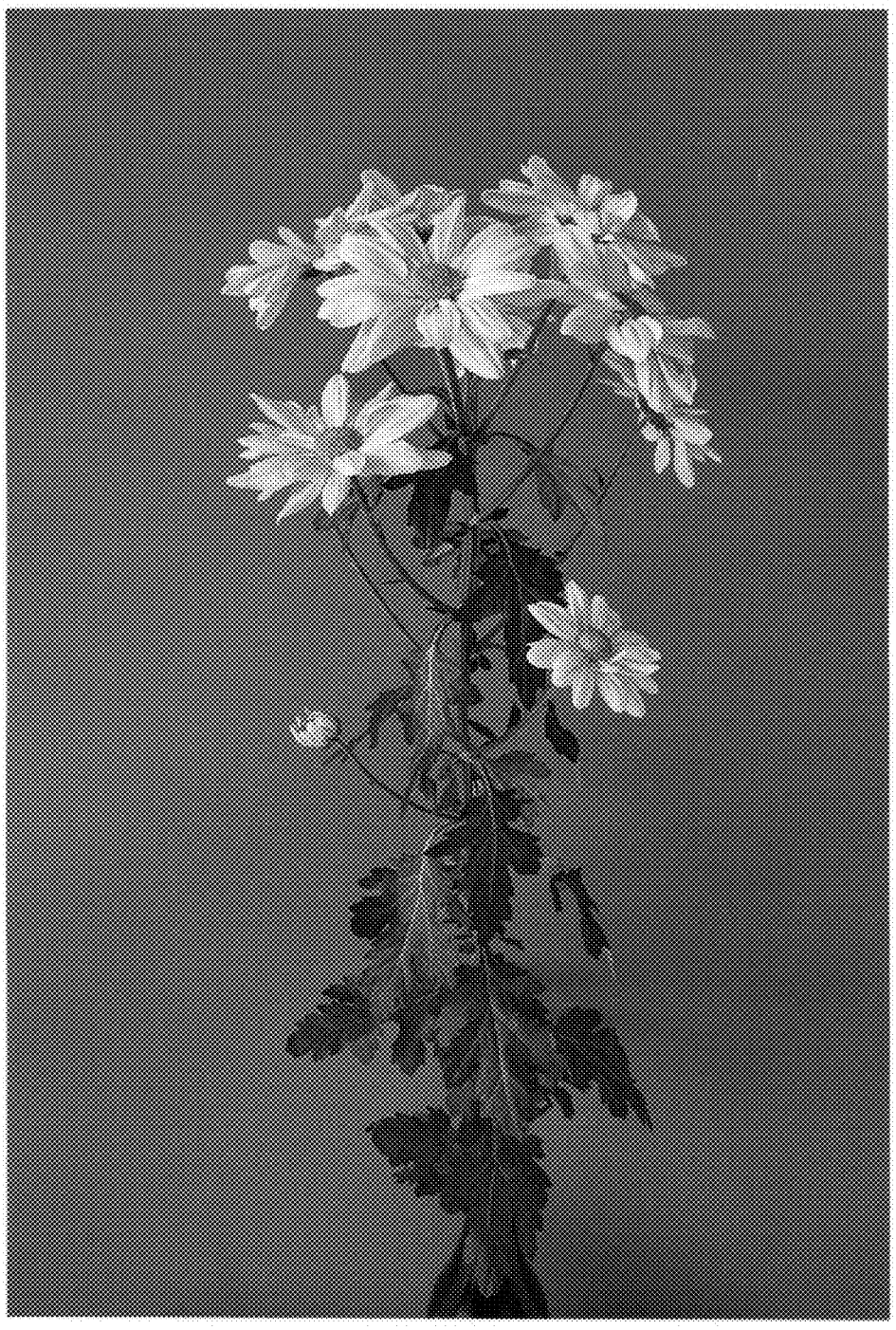

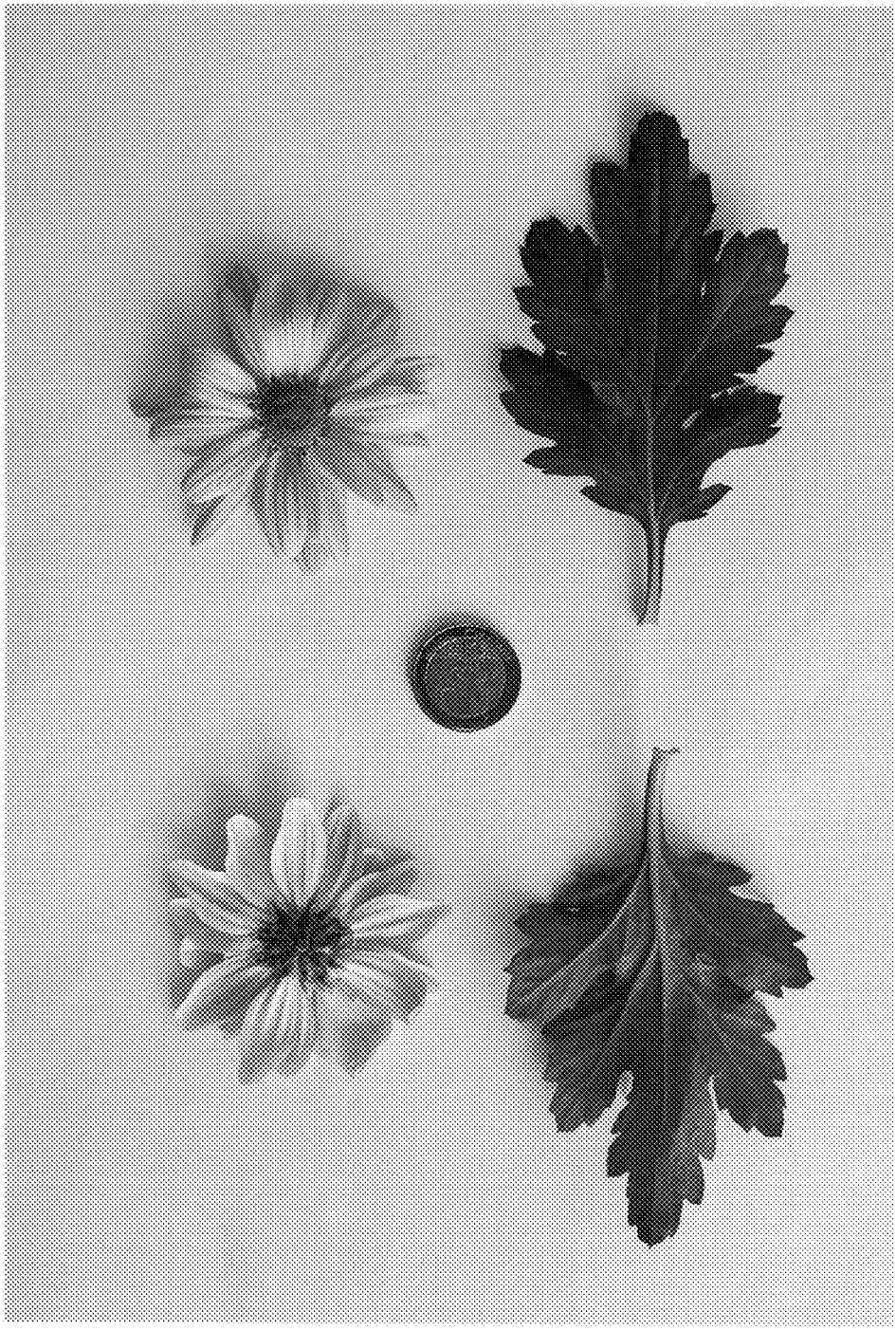

* * * * *